United States Patent [19]

Furukawa et al.

[11] Patent Number: 5,366,978
[45] Date of Patent: Nov. 22, 1994

[54] TREATMENT FOR KAWASAKI DISEASE

[75] Inventors: Susumu Furukawa; Tomoyo Matsubara, both of Tokyo, Japan

[73] Assignee: MK Medical Ltd., Tokyo, Japan

[21] Appl. No.: 145,137

[22] Filed: Nov. 3, 1993

[51] Int. Cl.$^5$ .............................................. A61K 31/52
[52] U.S. Cl. .................................................... 514/263
[58] Field of Search ................................. 514/263, 254

[56] References Cited

FOREIGN PATENT DOCUMENTS 5-124962  5/1993  Japan .

OTHER PUBLICATIONS

The Merck Index, Eleventh Edition (1989), p. 1586.

*Primary Examiner*—Zohreh Fay
*Attorney, Agent, or Firm*—Oblon, Spivak, McClelland, Maier & Neustadt

[57] ABSTRACT

Disclosed herein is a treatment for Kawasaki disease, which comprises administering a xanthine derivative represented by the general formula (1):

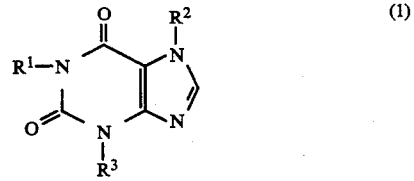

wherein at least one of $R^1$, $R^2$ and $R^3$ means a group expressed by $CH_3CO(CH_2)_n$—, in which n stands for a number of 1–5, and the remaining groups denote individually an alkyl group having 1–6 carbon atoms. The treatment can prevent the development of coronary lesions, which is the greatest problem of Kawasaki disease.

4 Claims, No Drawings

TREATMENT FOR KAWASAKI DISEASE

BACKGROUND OF THE INVENTION i) Field of the Invention

The present invention relates to a treatment for Kawasaki disease (acute febrile mucocutaneous lymph node syndrome).

ii) Description of the Background Art

Kawasaki disease is a trouble reported for the first time in 1967, is usually liable to attack infants of four years and downward, and shows symptoms that a patient is suddenly attacked by a high fever which lasts for 5 days or longer, the conjunctiva is congested, lips and a tongue turn crimson, the cervical lymph node is swollen, and a rash appears on the whole body. Although the mortality rate of Kawasaki disease is of the order of 1–2%, the greatest problem thereof is that coronary lesions remain as sequelae in 10–20% of the patients.

Although the cause of Kawasaki disease is not yet made clear, infection and immunity are the likeliest to participate in. Asteroid hormone therapy has heretofore been conducted as a treatment for this disease. However, steroid preparations often cause harmful side effects. In the case of Kawasaki disease in particular, a limitation is imposed on its application because the patients are infant.

On the other hand, a globulin therapy, namely, an intravenous drip of a human immunoglobulin preparation has been conducted recently. However, this therapy is very expensive and hence has involved a problem that a patient and its family have too many things on their hands. For example, if an infant of one-year old which has contracted Kawasaki disease is treated with a human immunoglobulin preparation, the expense amounts to about 200,000–400,000 yen in 5 days. Further, the effectiveness toward the prevention of the development of the sequelae, i.e., coronary lesions, which is the greatest problem in Kawasaki disease, is not fully satisfied.

SUMMARY OF THE INVENTION

It is therefore an object of the present invention to provide a treatment for Kawasaki disease, in particular, a treatment excellent in effect of preventing the development of coronary lesions which are sequelae.

In view of the foregoing circumstances, the present inventors have comparatively investigated concentrations of cytokine in sera as to many cases complicated by coronary lesions and cases with no complication in Kawasaki disease. As a result, it has been found that in the cases complicated by the coronary lesions, the amount of a tumor necrosis factor-α (hereinafter abbreviated as "TNF-α") in the sera increases to a remarkable extent. It has also been found that the concentration of this TNF-α is clearly reduced by administration of a xanthine derivative represented by the following general formula (1), a patient dosed with this derivative develops no coronary lesions, and the derivative scarcely causes side effects, leading to completion of the present invention.

In an aspect of the present invention, there is thus provided a treatment for Kawasaki disease, which comprises administering a xanthine derivative represented by the general formula (1):

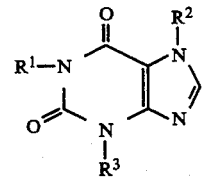

wherein at least one of $R^1$, $R^2$ and $R^3$ means a group represented by $CH_3CO(CH_2)_n-$, in which n stands for a number of 1–5, and the remaining groups denote individually an alkyl group having 1–6 carbon atoms.

The treatment according to the present invention can prevent the development of coronary lesions, which is the greatest problem of Kawasaki disease.

The above and other objects, features and advantages of the present invention will be readily appreciated from the preferred embodiments of the present invention, which will be described subsequently in detail.

DETAILED DESCRIPTION OF THE INVENTION AND PREFERRED EMBODIMENTS

The xanthine derivatives (1) useful in the practice of the treatment for Kawasaki disease according to the present invention are known compounds and are known to have effects of improving erythrocyte deformability, inhibiting platelet aggregation, increasing cerebral blood flow and improving cerebral metabolism, and other effects, and to be useful as remedies for cerebral circulation (for example, Japanese Patent Publication Nos. 21308/1970 and 22517/1979). For example, compounds of the general formula (1) in which $R^1$ is $CH_3CO(CH_2)_4-$, and $R^2$ and $R^3$ are methyl groups, and in which $R^1$ is $CH_3CO(CH_2)_4-$, $R^2$ is a n-propyl group and $R^3$ is a methyl group are sold under the common names of pentoxifylline and propentofylline, respectively. However, the effect of these xanthine derivatives (1) on Kawasaki disease has not been absolutely known.

As will be described subsequently in Examples, the xanthine derivatives (1) have an effect of reducing the concentration of TNF-α in a serum to a significant extent to prevent the development of coronary lesions. Besides, the compounds are widely used as remedies for cerebral circulation, scarcely cause side effects and also are high in safety.

The xanthine compound (1) can be administered as it is or together with a conventional carrier for preparation. No particular limitation is imposed on the form of the administration. In consideration of the fact that most of cases of Kawasaki disease are infants up to 4 years, however, oral preparations such as tablets, granules, syrups and dry syrups, and parenteral preparations such as injections and suppositories may be mentioned as forms for preparations. Of these, oral preparations are preferred. Various components such as vitamin preparations and amino acids may be incorporated as needed.

In the present invention, these preparations may be formulated in accordance with methods known per se in the art. For example, a tablet preparation is formulated by mixing the xanthine derivative (1) with additives such as gelatin, starch, milk sugar, magnesium stearate and gum arabic. A syrup preparation is formulated by mixing the xanthine derivative (1) with an edulcorant such as sucrose, and an antiseptic, colorant, flavor and/or the like The dose of the xanthine derivative (1) in the treatment according to the present invention varies according to the age, weight and diseased condition of a patient to be dosed, and the like. However, it is preferable to dose the derivative (1) in a proportion of 2-20 mg/kg/day. A preference is also given to a dosing method in which the above-described dose of the xanthine derivative (1) is administered once a day or in several portions.

The present invention will hereinafter be described in more detail by the following examples. However, it should be borne in mind that this invention is not limited to and by these examples only. Example 1

Pentoxifylline was administered to five cases of Kawasaki disease to determine the concentrations of TNF-α in respective sera, followed by examination as to whether they developed coronary lesions or not.

Incidentally, pentoxifylline was orally dosed for 6 days in two portions in a proportion of 6-10 mg/kg/day. The concentration of TNF-α in the serum was determined by means of a commercially-available kit in accordance with the sandwich ELISA making use of two monoclonal antibodies.

The thus-obtained results are shown in Table 1.

nary lesions was prevented. No side effects by the administration of pentoxifylline were observed.

What is claimed is:

1. A treatment for Kawasaki disease, which comprises administering an amount effective to prevent coronary lesions, of a xanthine derivative represented by the general formula (1):

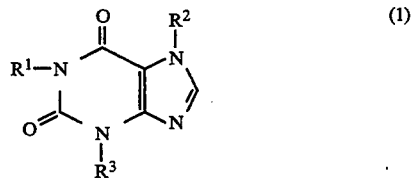

wherein at least one of $R^1$, $R^2$ and $R^3$ means a group expressed by $CH_3CO(CH_2)_n-$, in which n stands for a number of 1-5, and the remaining groups denote individually an alkyl group having 1-6 carbon atoms.

2. The treatment according to claim 1, wherein the xanthine derivative (1) is pentoxifylline or propentofylline.

3. The treatment according to claim 1, wherein the dosing method is an oral administration.

4. The treatment according to claim 1 wherein the xanthine derivative is dosed in an amount of 2-20 mg/kg/day.

TABLE 1

| Case No. | Age and sex | Dose (mg/kg/day) | Dosing period (day) | Concentration of TNF-α in serum (pg/ml) | | Development of coronary lesion |
|---|---|---|---|---|---|---|
| | | | | Before dosing | After dosing | |
| 1 | Six-month, Female | 6 | 6 | 17.4 | <3.4 | None |
| 2 | One-year and eight-month, Female | 6 | 6 | 13.4 | 5.5 | None |
| 3 | One-year and four-month, Male | 6 | 6 | 11.8 | <3.4 | None |
| 4 | Three-year and nine-month, Male | 6 | 6 | 5.9 | <3.4 | None |
| 5 | Seven-month, Male | 6 | 6 | 12.5 | 4.4 | None |

As apparent from Table 1, by the administration of pentoxifylline, the concentrations of TNF-α in the sera were clearly reduced, and the development of the coro-